United States Patent [19]

Yim

[11] Patent Number: 5,304,495

[45] Date of Patent: Apr. 19, 1994

[54] METHOD FOR DETERMINING FLUSH INTERFERENCE IN MEASUREMENT OF CHEMICAL AND PHYSICAL PARAMETERS WITH INDWELLING PROBE

[75] Inventor: Jeffrey B. Yim, Honolulu, Hi.

[73] Assignee: Abbott Laboratories, Abbott Park, Ill.

[21] Appl. No.: 997,863

[22] Filed: Dec. 29, 1992

[51] Int. Cl.[5] .................... G01N 25/20; G01N 33/48; G01N 33/50; A61B 5/02

[52] U.S. Cl. ..................................... 436/68; 128/634; 128/673; 356/41; 422/82.12; 422/83; 436/34; 436/147; 436/163

[58] Field of Search .............. 436/11, 34, 68, 147, 436/148, 163, 181; 422/82.12, 82.13, 93, 83, 68.1; 128/633, 634, 664, 665, 673; 356/39, 41

[56] References Cited

U.S. PATENT DOCUMENTS

| | | | |
|---|---|---|---|
| 4,907,857 | 3/1990 | Giuliani et al. | 350/96.29 |
| 5,047,627 | 9/1991 | Yim et al. | 250/227.23 |
| 5,058,416 | 10/1991 | Engelhardt et al. | 73/19.01 |
| 5,119,463 | 6/1992 | Vurek et al. | 385/129 |
| 5,134,998 | 8/1992 | Tusa et al. | 128/632 |
| 5,166,990 | 11/1992 | Riccitelli et al. | 385/12 |

OTHER PUBLICATIONS

Burnett et al., "Tentative Standard for Definitions of Quantities and Conventions Related to Blood pH and Gas Analysis," National Committee for Clinical Laboratory Standards (NCCLS) Publication; vol. 2, No. 10, Published Aug. 1982, ©1982, pp. 336–350 (plus cover sheet).

*Primary Examiner*—Robert J. Warden
*Assistant Examiner*—Robert Carpenter
*Attorney, Agent, or Firm*—Christensen, O'Connor, Johnson & Kindness

[57] ABSTRACT

A system (10) for in vivo measuring chemical and physical parameters of a patient's blood includes a probe (12), a sensing system (14), and flush interference warning devices (20). The system measures pH, $pCO_2$, and temperature values, and determines a base excess value using the measured pH and $pCO_2$. The time rate of change of the base excess value is also determined, as is the time rate of change of temperature. The warning devices are activated, indicating that the measured parameters are likely affected by the presence of flush solution flowing past the probe, when either: (a) the base excess value is less than a predefined threshold base excess; (b) the absolute value of the time rate of change of the base excess value is greater than a predefined threshold time rate of change of base excess; or, (c) the absolute value of the time rate of change of temperature is greater than a predefined threshold time rate of change of temperature.

16 Claims, 13 Drawing Sheets

METHOD FOR DETERMINING FLUSH INTERFERENCE IN MEASUREMENT OF CHEMICAL AND PHYSICAL PARAMETERS WITH INDWELLING PROBE

FIELD OF THE INVENTION

The present invention relates to methods for in vivo monitoring of a patient's chemical and physical bodily parameters utilizing indwelling probes, and more particularly, to methods for detecting conditions likely to cause errors in the in vivo measurement of blood properties.

BACKGROUND OF THE INVENTION

Chemical sensors have been developed in recent years for the in vivo monitoring of the concentration of various analytes, including oxygen, carbon dioxide, and hydrogen ions (i.e., pH), in liquids and gases. In particular, fiber-optic chemical sensors have been developed for measuring the levels of carbon dioxide and oxygen gases in the blood, and the pH of the blood. Such sensors typically include one or more optical fibers, on the distal end of which are mounted analyte sensors. These sensors exhibit a perturbed light absorbance, luminescence, or phosphorescence in the presence of the analyte molecules. A thermocouple may be included with these analyte sensors, the combination being configured as a probe that is insertable through a catheter into a patient's vascular system.

A saline flush solution that may contain an anti-clotting agent is often introduced through the inserted catheter at a low rate, such as 3 to 5 ccs per hour, to prevent the development of thrombi around the probe. Signals affected by the analyte sensors mounted at the distal end of the probe are periodically monitored to determine the patient's blood gas levels and temperature of the blood.

Sufficient blood flow past the probe is required to clear this saline flush solution from the vicinity of the sensors and enable a measurement of pH and the partial pressure of carbon dioxide ($pCO_2$) and oxygen ($pO_2$) that is accurately reflective of these analyte concentrations in the bloodstream. A problem with the accuracy of blood chemistry measurements may be experienced when certain diseases or physiological states cause a reduction in the amount of blood flow through the monitored blood vessel. Causal factors of slow peripheral blood flow include thoracic surgical procedures, cold extremities, left-side heart failure, arterial sclerosis, local vasoconstriction due to catheterization, and occlusion of the blood vessel by the catheter through which the probe is inserted.

When blood flow past the probe is reduced, the saline flush solution is not fully cleared away from the chemical sensors by the blood flow, and the volume of blood surrounding the chemical sensors is diluted. Consequently, the chemical sensors in the probe measure pH, $pCO_2$, $pO_2$, and temperature of a mixture of blood and saline flush, rather than systemic blood. During such periods of "flush interference" (i.e., blood mixed with substantial quantities of saline flush), the chemical sensors provide measurements that are not clinically relevent. Saline flush solution typically is characterized by pH and $pCO_2$ values that are substantially lower than the corresponding values of systemic blood, and its $pO_2$ may vary greatly from that of systemic blood value at any given time. Erroneous readings caused by flush interference may, at best, cause medical personnel to disregard data from the chemical sensors. When data from the probe cannot be relied upon, the practitioner is often required to draw and analyze a discrete blood gas sample from the patient. Potentially more harmful, medical personnel may instead not recognize the flush interference condition and determine patient treatment based upon the erroneous results.

Clinical and animal trails have shown that peripheral arterial blood flow compromises saline flush solution approximately 5 to 30% of the time during in vivo measurements of blood gas parameters. The prior methodology for recognizing that flush interference is occurring has been to watch for extreme drops in both the measured pH (such as a measured pH less than 7.0) and $pCO_2$ (such as a measured $pCO_2$ below 10 torr). Such low measurements are indicative of chronic flush interference, i.e., dilution of blood with substantial quantities of flush solution for the period of time during which the blood gas parameters are measured. Because there are few, slow onset disease states, such as chronic metabolic acidosis, that can cause this combination of low arterial pH and $pCO_2$, diagnosis of chronic flush interference is relatively easy. However, in cases of intermittent or less extreme flush interference, the resulting discrepancies in measured pH and $pCO_2$, as well as $pO_2$ and temperature, are not as readily identified. In cases of significant but non-chronic flush interference, erroneous readings may either go undetected, or if detected, may result in the need for discrete blood sample analysis, with ensuring cost, delay, and potential patient discomfort.

SUMMARY OF THE INVENTION

The present invention provides a method and system for determining interference during the in vivo measurement of chemical or physical parameters using an indwelling probe, such interference being caused by the introduction of a flush fluid flowing past the probe. The method includes the steps of periodically measuring a bodily chemical or physical parameter, wherein the measured parameter is susceptible to influence by dilution with flush fluid. A time rate of change of the measured parameter is then calculated, and the calculated time rate of change is compared with a threshold time rate of change. A warning output device is activated when the calculated time rate of change of the measured parameter exceeds the threshold time rate of change.

In a preferred embodiment of the invention, the indwelling probe measures both pH and the partial pressure of carbon dioxide ($pCO_2$). A base excess value is computed from the measured pH and $pCO_2$. The calculated base excess is compared to a threshold base excess value. If the calculated base excess is less than the threshold base excess, the warning output device is activated. This comparison has been found effective for identifying periods of chronic flush interference.

In addition to comparing the base excess value, in the preferred embodiment of the present invention, the time rate of the calculated base excess is also computed and compared to a threshold time rate of change. If the absolute value of the computed time rate of change of the base excess is greater than a threshold time rate of change of the base excess, the warning output device is activated. Calculation and comparison of the time rate of change of the base excess has been found effective for accurately identifying instances of intermittent flush interference.

Finally, in addition to computing and comparing base excess values and the time rate of change of base excess values, the preferred embodiment of the present inventive method also includes the calculation of a time rate of change of temperature measured by the probe. If the absolute value of the time rate of change of measured temperature exceeds a threshold time rate of change of temperature, the warning output device is also activated. Thus, the warning output device is activated if either the base excess, time rate of change of base excess, or time rate of change of measured temperature is found to fall above or below certain predetermined limits.

Apparatus for providing a warning when a flush fluid interferes with the accuracy with which a plurality of parameters of a patient's blood are monitored, for use in a system for in vivo monitoring of the parameters, is another aspect of the present invention. The apparatus includes elements that implement functions generally consistent with the steps of the method discussed above.

The present invention is thus directed to both a method and apparatus for identifying periods of flush interference and providing a warning to medical personnel that potentially inaccurate values of blood parameters may have been obtained during measurements of the those parameters due to the effect of the flush interference. Medical personnel are thus able to recognize when data from the analyte chemical sensors should be disregarded, without requiring frequent discrete blood sample analysis conducted solely to confirm the probe readings. The potential for basing treatment on discrepant data is accordingly also lessened.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

In an application using a preferred embodiment of the present invention, a blood gas monitoring probe is inserted via a catheter into a patient's radial artery to measure blood gas parameters, including pH and $pCO_2$. The probe additionally measures the $pO_2$ and temperature of the blood. A base excess value is determined using a procedure well known to those skilled in the field, as described more fully hereinbelow. The time rate of change of the base excess is also determined, as is the time rate of change of the measured temperature. An alarm device is activated, indicating flush solution interference with accurate blood property measurements, if either: (a) the calculated base excess value is less than a threshold base excess value; (b) the absolute value of the calculated time rate of change of the base excess is greater than a threshold time rate of change of the base excess; or (c) the absolute value of the calculated time rate of change of temperature is greater than a threshold time rate of change of temperature.

Figure 1:
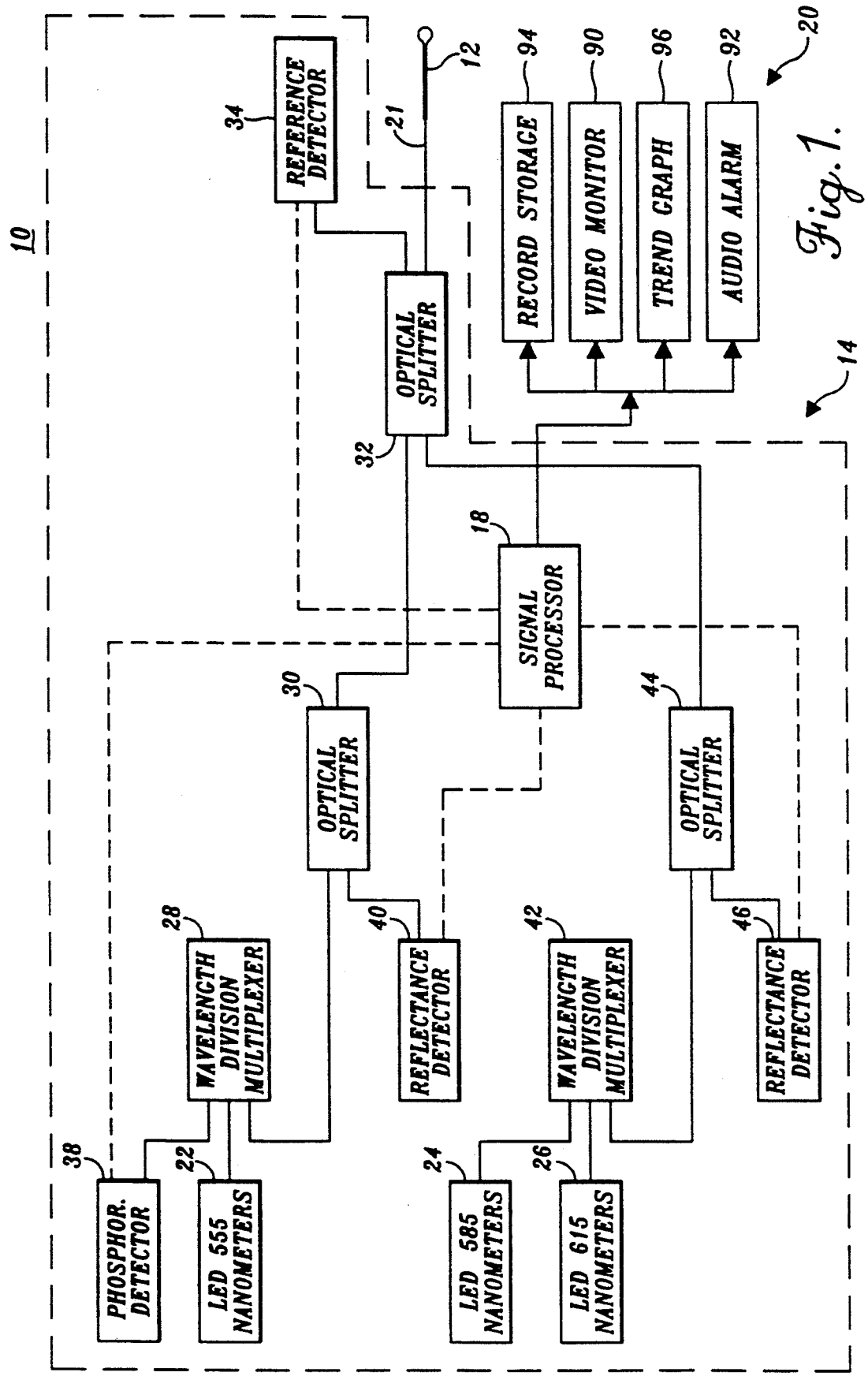
FIG. 1 is a block diagram of a system for blood gas measurement and identification of flush interference, in accordance with the present invention.

A blood gas measurement system 10 using the method of the present invention is shown in block diagram form in FIG. 1. System 10 uses a multiparameter probe 12 and sensing system 14 for determining pH, $pCO_2$, and $pO_2$. Sensing system 14 includes a signal processor 18 for determining when the measurements from probe 12 indicate a condition of flush interference, using the method of the present invention. If flush interference is detected, signal processor 18 activates one or more visual and/or audible alarm devices 20 to warn the operator that the data produced by the system 10 has been affected by flush interference.

The method and apparatus of the present invention is suitable for use with a variety of intravascular probes that monitor chemical and physical blood parameters. In particular, the present invention is suitable for use with an in vivo probe that measures pH, $pCO_2$, and $pO_2$), and the temperature of blood. One such probe believed to be suitable for use with the present invention is described in commonly assigned U.S. Pat. No. 5,119,463 to Vurek et al., entitled COMPOUND OPTICAL PROBE EMPLOYING SINGLE OPTICAL WAVE GUIDE, issued on Jun. 2, 1992, the disclosure and drawing figures of which are hereby expressly incorporated herein by reference.

As disclosed in this patent, probe 12 comprises a single optical wave guide 21 having a longitudinal axis along which light signals at a plurality of wavelengths propagate bi-directionally. Sensing system 14 produces light signals at selected wavelengths. The extent by which light signals produced by sensing system 14 are absorbed by two analyte sensors included in probe 12 is respectively dependent upon the partial pressure of carbon dioxide and the pH of the blood in which the probe is immersed. A third analyte sensor disposed at the distal end of the probe phosphoresces when excited by light of one of the selected wavelengths, and the decay time of the phosphorescence is a function of the partial pressure of oxygen in the blood.

More specifically, sensing system 14 includes three light emitting diodes (LEDs) 22, 24, and 26 that produce pulse light signals at wavelengths of 555 nanometers, 585 nanometers and 615 nanometers, respectively. These light signals are conveyed to prove 12 via wave guide 21. For measurement of $pO_2$, the signal produced by LED 22 is directed to a wavelength division multiplexer 28 that filters wavelengths in the red region from the signal. The filtered signal is transmitted to an optical splitter 30, and then to a second optical splitter 32. From optical splitter 32, a portion of the signal is directed to a reference detector 34. Reference detector 34 produces a reference signal that is used to compensate for variations in the output of LED 22. The remainder of the signal from optical splitter 32 is transmitted via wave guide 21 to probe 12. This signal causes an oxygen sensitive material, porphyrin, which is included in a polymer matrix formed about the distal end of probe 12 to phosphoresce. Phosphorescence of the oxygen indicator material produces light having a wavelength of 650 nanometers. As noted above, the time profile of the phosphorescent decay of this emitted light is dependent upon the partial pressure of oxygen around probe 12.

The emitted light is conveyed by optical wave guide 21 to optical splitter 32 and optical splitter 30. The light signal is then transmitted to multiplexer 28, which filters out light in the green region. The filtered signal is directed to a phosphorescence detector 38, causing it to produce a corresponding electrical signal. The electrical signal from phosphorescence detector 38 is then conveyed to signal processor 18, which measures the phosphorescence decay profile in order to determine the $pO_2$ value in the blood at that time.

For measurement of the partial pressure of carbon dioxide, a signal from LED 22 is similarly transmitted to probe 12. This signal passes through a sensor pellet 40 mounted at the distal end of probe 12, which includes a $CO_2$ sensitive indicator, such as phenol red. The light pulse is attenuated as a function of the partial pressure of $CO_2$ in the blood surrounding the probe. Attenuated light is reflected from a mirror surface on the distal side of the pellet, back into wave guide 21, and is directed to optical splitter 32 and optical splitter 30, and then to a reflectance detector 40. Reflectance detector 40 measures the amplitude of the reflected signal and sends the signal to signal processor 18. The signal processor determines the $pCO_2$ of the blood.

For pH determination, LED 24 produces a pulse light signal that is directed through a wavelength division multiplexer 42, and then to an optical splitter 44 and to optical splitter 32. A portion of the signal from optical splitter 32 is split is transmitted to reference detector 34, which is used to compensate for variations in the output of LED 24. The remaining portion of the signal from optical splitter 32 is directed to probe 12. This light pulse is attenuated by a pH sensor pellet that comprises a pH sensitive indicator, such as phenol red, to an extent dependent on the pH level in the blood surrounding the probe. Attenuated light is reflected back into optical wave guide 21 from a mirror surface on the pH sensor pellet.

The combined reflected light from the $CO_2$ sensor pellet and pH sensor pellet is transmitted by wave guide 21 to splitter 32, and splitter 44. The signal from splitter 44 is directed to a reflectance detector 46, which measures the amplitude of the combined reflected signal. The amplitude thus determined is then sent to the signal processor 18, which computes the pH level of the monitored bloodstream by removing the portion of the reflected light contributed by the $CO_2$ sensor pellet.

LED 26 produces a signal that is transmitted to probe 12 for path normalization. Probe 12 also includes a thermocouple (not separately illustrated), which produces an electrical signal proportional to the temperature of the monitored bloodstream that is transmitted to signal processor 18 over a pair of conductors (not shown). The construction and operation of probe 12 and sensing system 14 as thus far described is more fully described in the above-referenced patent.

While probe 12 and sensing system 14 are believed to be suitable for implementing the method of the present invention, it should be understood that this invention is equally well suited for use with other multi-parameter chemical sensing probes and sensing systems. For example, another suitable probe and sensing system is disclosed by U.S. Pat. No. 5,047,627 ("'627") to Yim et al., entitled CONFIGURATION FIBER-OPTIC BLOOD GAS SENSOR BUNDLE AND METHOD OF MAKING, the disclosure of which is hereby expressly incorporated by referenced. The Yim et al. '627 probe is proven to be well suited for use with the present invention, and may be preferred due to the increased breakage-resistance imparted by the multi-optical conductor bundle. The probe disclosed in Yim '627 includes a separate optical conductor for each of the $pCO_2$, pH and $pO_2$ analyte indicators, as well as a corresponding signal detector included in the sensing system for reading each analyte indicator.

Figure 2A:
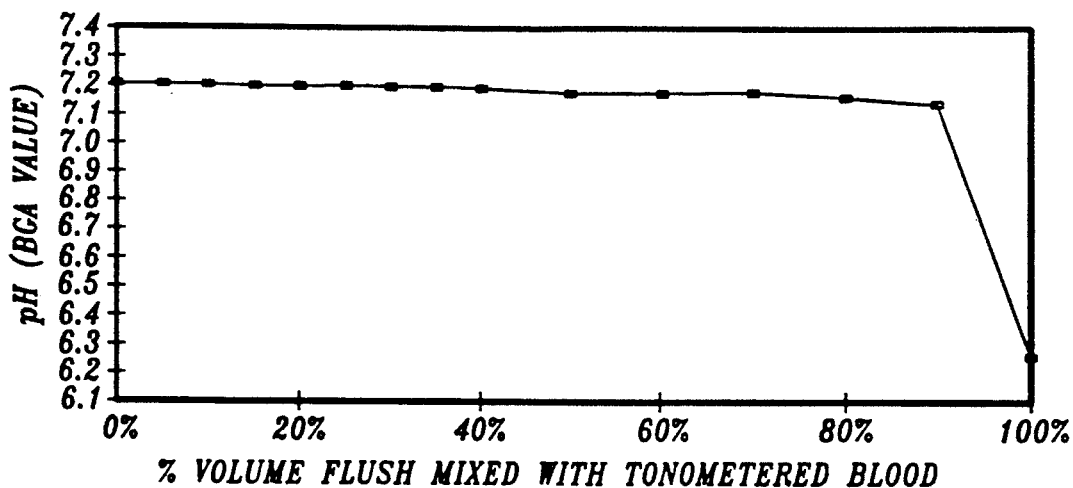
FIGS. 2A, 2B, and 2C are graphs showing the effect of varying percentages of saline flush mixed with tonometered blood on measured pH, $pCO_2$, and $pO_2$, respectively.
Figure 2B:
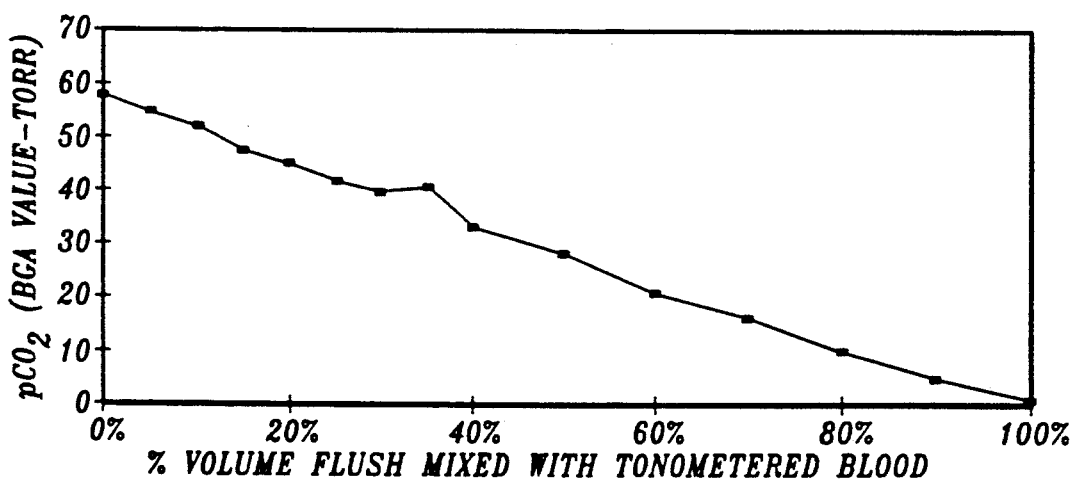
Figure 2C:
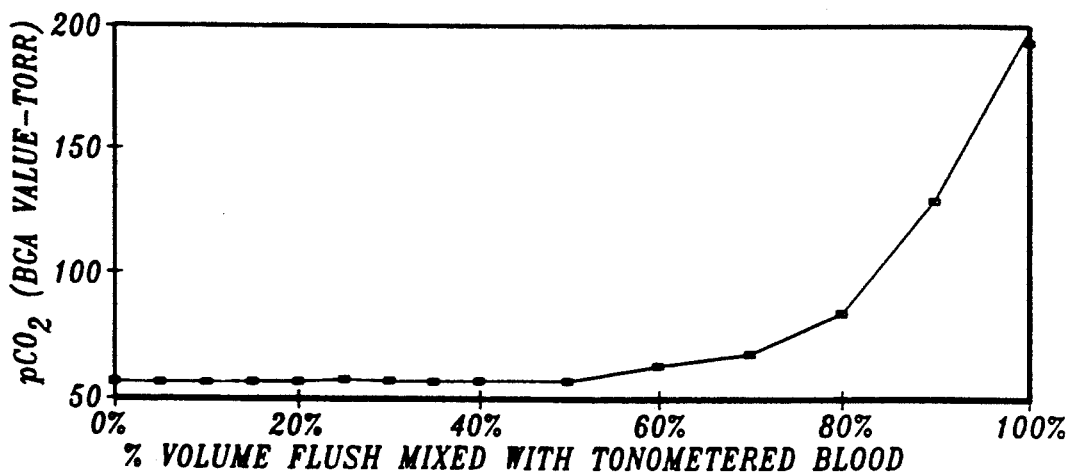

In order to quantify the effect of flush solution dilution on measured blood gas values, tonometry experiments were conducted wherein blood of known gas content was mixed with various percentages of saline flush solution. The mixtures were analyzed using a Corning Model 178 blood gas analyzer. The effects of saline concentration on the measured parameters of pH, $pCO_2$ and $pO_2$ are shown in FIGS. 2A, 2B, and 2C, respectively. As shown in FIG. 2A, significant deviation in the measured pH does not occur until the blood is diluted with greater than 80% saline flush. Referring to FIG. 2C, measured $pO_2$ is not substantially affected until the blood is diluted with in excess of 50% saline flush. However, referring to FIG. 2B, the presence of saline flush at levels greater than 10% greatly affects the measured $pCO_2$.

Conventional chemical sensor probes inserted arterially through a catheter typically have a flush flow rate of 3 to 5 ccs per hour. Given this flush flow rate and the noted affect of low levels of flush solution dilution on measured $pCO_2$, arterial blood flow rates of 45 ccs per hour or less potentially may represent a condition in which flush interference with measured parameters becomes significant. Normal radial artery blood flow rates are known by those of skill in the art to be about 35 to 100 ccs per minute (2,100 to 6,000 ccs per hour), far in excess of the blood flow rate calculated to represent a potential flush interference problem. Thus, significant flush interference is seen only when the blood flow rate in the radial artery is severely limited. The effects of flush interference in other size blood vessels with substantially lower normal blood flow rates may be more readily evident.

Analysis of clinical cases where blood gas was analyzed using the above-described probe 12 and sensing system 14 has determined that the chemical sensors of probe 12 may be used to identify episodes of flush interference by taking advantage of the differential buffering capacities of saline flush solution and blood. Blood has four acid/base buffers: the equilibria established by $CO_2$ and bicarbonate; the buffering capacity of hemoglobin; the tertiary buffering system comprised of blood proteins; and the phosphate buffer system. Saline flush solution has no such buffering capacity, however. The pH of saline solution is almost always less than 6.6, and typically about 6.2. The pH of blood, however, ranges from about 7.1 to about 7.6, and for the average patient, is about 7.4. Thus, as the blood around probe 12 becomes diluted with flush, the pH of the solution becomes more acidic, i.e., the pH decreases.

Similarly, the partial pressure of $CO_2$ in saline is approximately zero torr. The partial pressure of $CO_2$ in arterial blood is dependent upon the respiratory and acid/base status of the patient. Typically, the $pCO_2$ of arterial blood ranges between 15 and 80 torr, and for the average patient is about 40 torr. Dilution with saline flush increases the fluid volume surrounding the probe without increasing the total $CO_2$ content. Thus, dilution with flush solution results in a measured $pCO_2$ that is well below that of systemic blood.

The oxygen content of saline flush solution is about 180 torr at 22° C. The partial pressure of oxygen in arterial blood is extremely dynamic, and can range between from about 30 to 600 torr. Thus, for systemic arterial oxygen concentrations below 150 torr, dilution with flush solution results in a noticeable increase in the measured $pO_2$. Conversely, at systemic arterial blood oxygen concentrations greater than about 200 torr, dilution with flush solution results in a decrease in the measured $pO_2$. This divergent behavior is complicated by hemoglobin's affinity for oxygen, since the binding efficiency of hemoglobin is dependent upon temperature, pH, and other variables.

In summary, when systemic blood is diluted with a flush solution, probe 12 tends to read pH and $pCO_2$ levels that are lower than that of systemic blood, and $pO_2$ values that tend towards 180 torr. Attempts to establish cutoffs for absolute pH and $pCO_2$ levels as indicators of flush interference have been found to be unreliable due to the variability of systemic blood pH and $CO_2$ levels.

In vivo data obtained using the previously described probe 12 and sensing system 14 showing the results of intermittent flush interference on the measurement of pH, $pCO_2$, $pO_2$, and temperature are shown in FIGS. 3A, 3B, 3C, and 3D, respectively. For each of FIGS. 3A, 3B, and 3C, discrete blood samples were periodically taken, and Corning Model 178 blood gas analyzer was used to measure the parameters for comparison against corresponding measurements made with probe 12; the results of these analyses are shown as discrete points on the charts. Discrete blood gas analysis was performed both on-site in an intensive care unit (ICU) and off-site at a lab. For example, referring to FIG. 3A, the solid line represents pH measurements taken every 10 seconds using probe 12. The discrete data points on the chart indicate the median pH measured using discrete blood gas analysis in ICU, the median pH measured using discrete blood gas analysis at the lab, and the maximum and minimum blood gas analysis values found by either the ICU or lab analysis. The same approach was followed for the $pCO_2$ and $pO_2$ measurements of FIGS. 3B and 3C. For the temperature measurements of FIG. 3D, discrete measurements of the patient's temperature taken externally are also shown for comparison with the blood temperature indicated by probe 12.

Figure 3A:
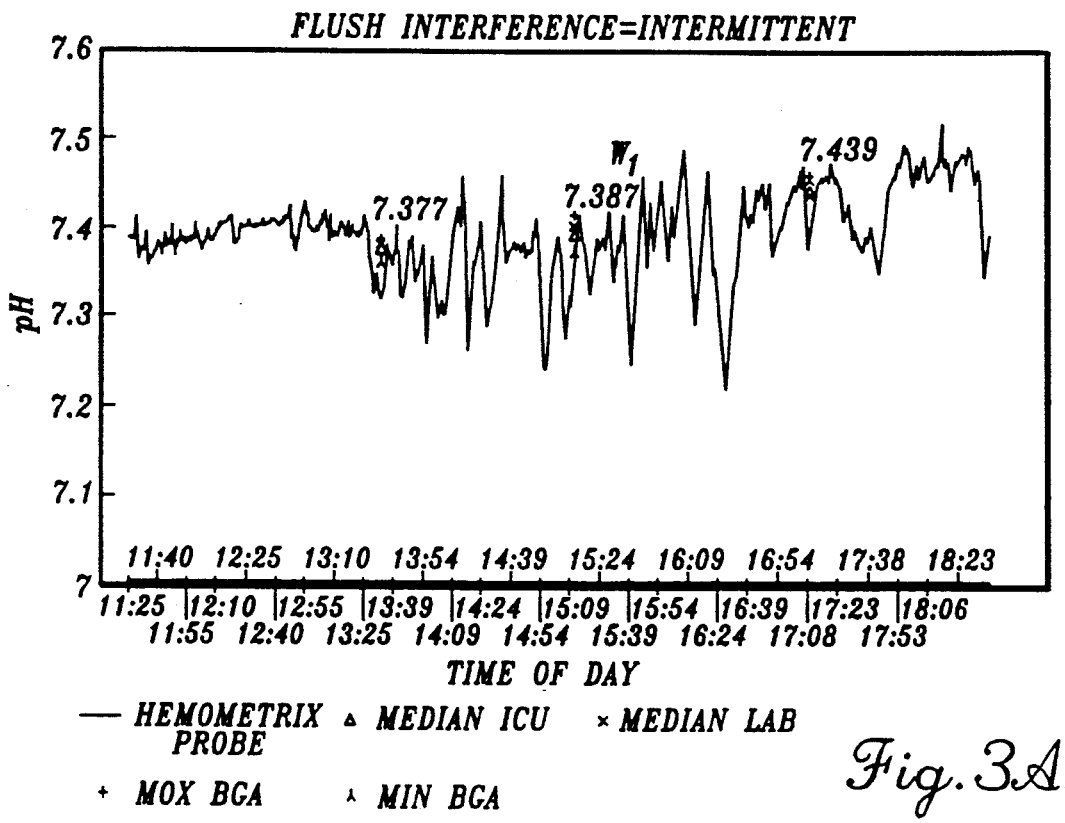
FIGS. 3A, 3B, 3C and 3D are charts showing the effect of intermittent flush interference on measured pH, $pCO_2$, $pO_2$, and temperature, respectively, versus time.
Figure 3B:
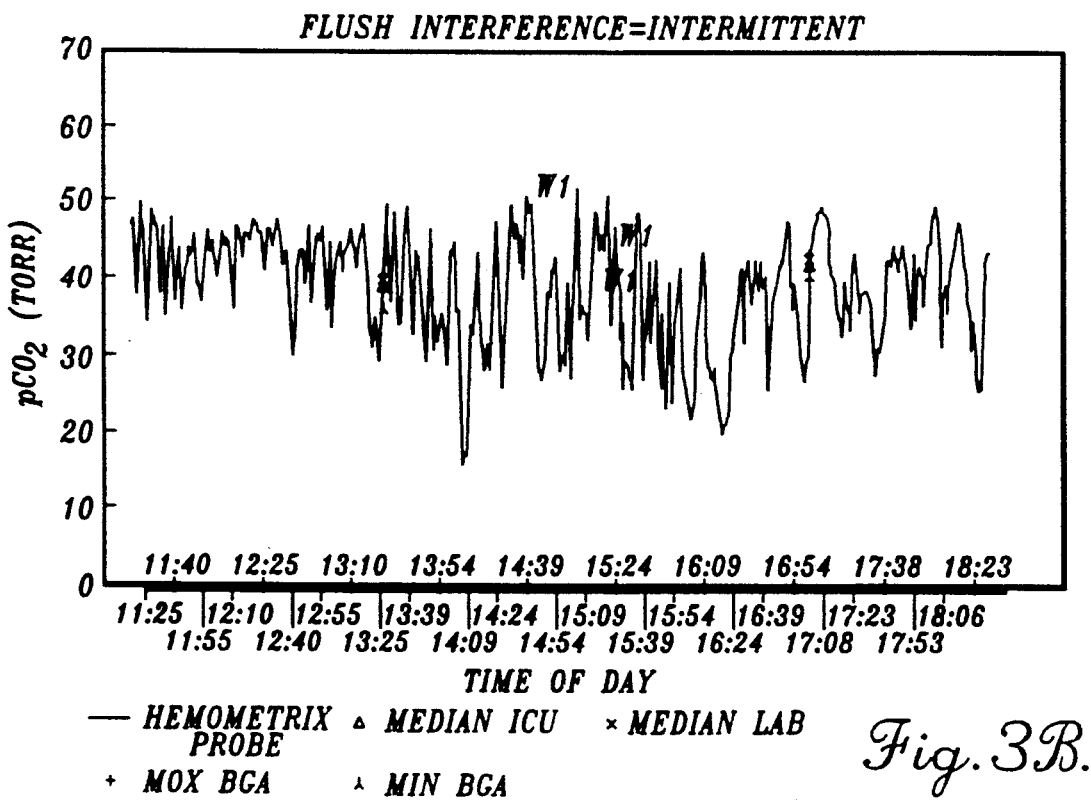
Figure 3C:
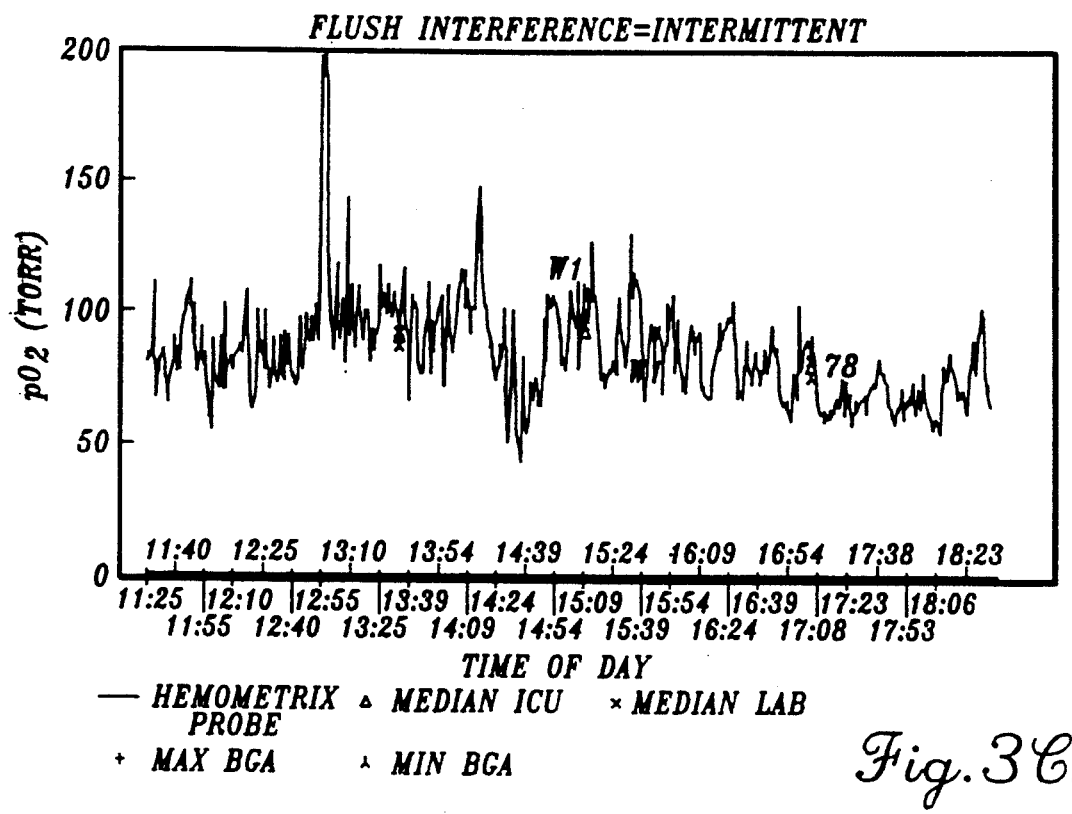
Figure 3D:
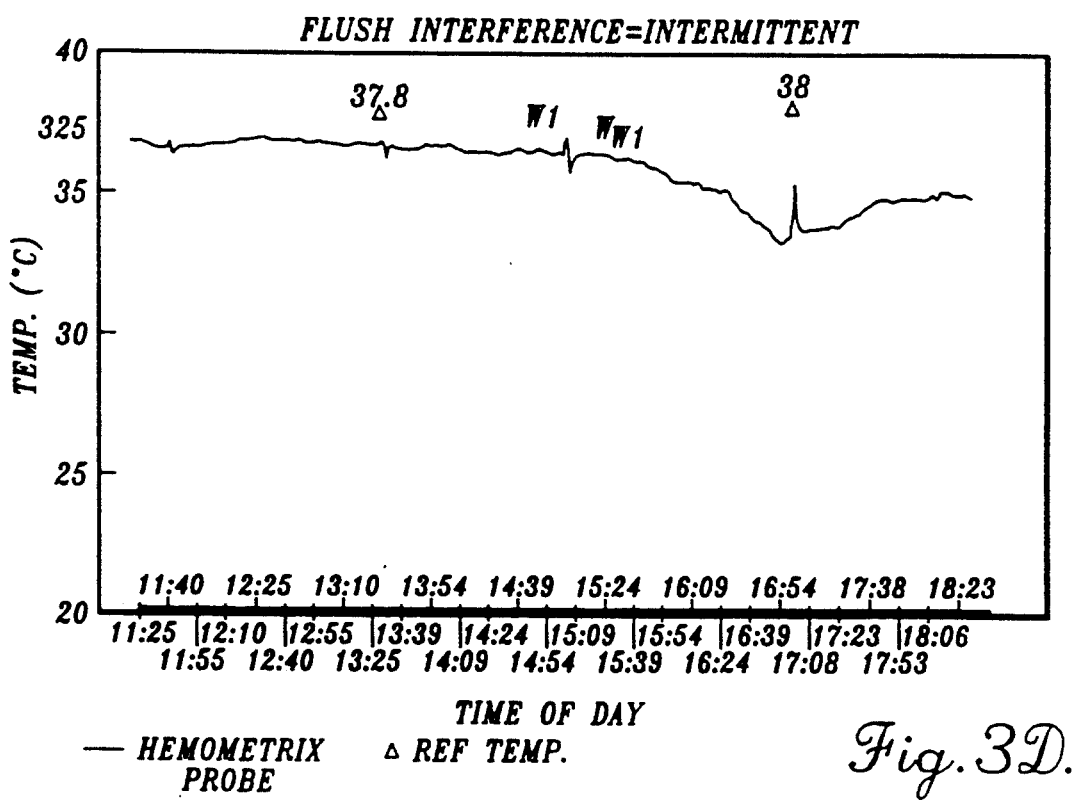

For the pH and $pCO_2$ charts of FIGS. 3A and 3B, the values measured by probe 12 are intermittently significantly lower than those measured through blood gas analysis, indicating the effect of intermittent flush interference. While the discrete blood gas analysis samples are relatively constant over the duration of the monitored time, the output from probe 12 is very dynamic or noisy, indicative of short duration exposure to flush-diluted blood, interspersed with periods of higher rates of blood flow, wherein the flush solution is swept away from the probe.

FIGS. 4A, 4B, 4C, and 4D represent additional clinical data obtained using probe 12 and confirmatory blood gas analysis showing the effect of chronic flush interference for pH, $pCO_2$, $pO_2$, and temperature, respectively. As used herein, the term "chronic" flush interference refers to long duration dilution with substantial quantities of saline flush solution. The discrete blood gas analysis samples are seen to differ significantly from the samples obtained using probe 12, particularly for the pH, $pCO_2$, and temperature measurements. The large negative pH and $pCO_2$ bias is a typical "signature" response of chronic flush interference. The significant decrease in measured temperature is due to the difference in the temperature of discrete arterial blood (approximately 37° C.), and the temperature of the saline flush solution, which is at ambient room temperature.

Another situation in which the presence of flush solution interferes with accurate measurements by probe 12 is during "fast flush," wherein medical personnel clear the arterial catheter line of blood by introducing a bolus of saline. During the short time that this fast flush clears blood away from the chemical sensors of probe 12, the probe measures the parameters of the flush solution, rather than the parameters of the systemic blood. FIGS. 5A, 5B, 5C, and 5D indicate the effect of fast flushes on the measured pH, $pCO_2$, $pO_2$, and temperature, respectively. The downward spikes in the pH, $pCO_2$, and temperature measurements taken by probe 12, as well as the upward spikes in the $pO_2$ measurements (since $pO_2$ was less than 180 torr), are artifacts introduced by fast flushes.

Because of the strong response of pH and $pCO_2$ measurements to flush interference, these measurements serve as the basis of the present inventive method for detecting flush interference. As shown in FIGS. 3A and 3B, the pH and $pCO_2$ measurements by probe 12 change rapidly in response to intermittent flush interference. Thus, the time rate of change, i.e., the first derivative with respect to time, of measured pH and measured $pCO_2$ can serve as a warning of intermittent flush interference. Likewise, the calculated value of bicarbonate and time rate of change of bicarbonate can be used to warn of intermittent flush interference. Particularly, a large negative time rate of change of measured pH, coupled with a large negative rate of change of measured $pCO_2$, can provide an early warning of flush interference.

Figure 4A:
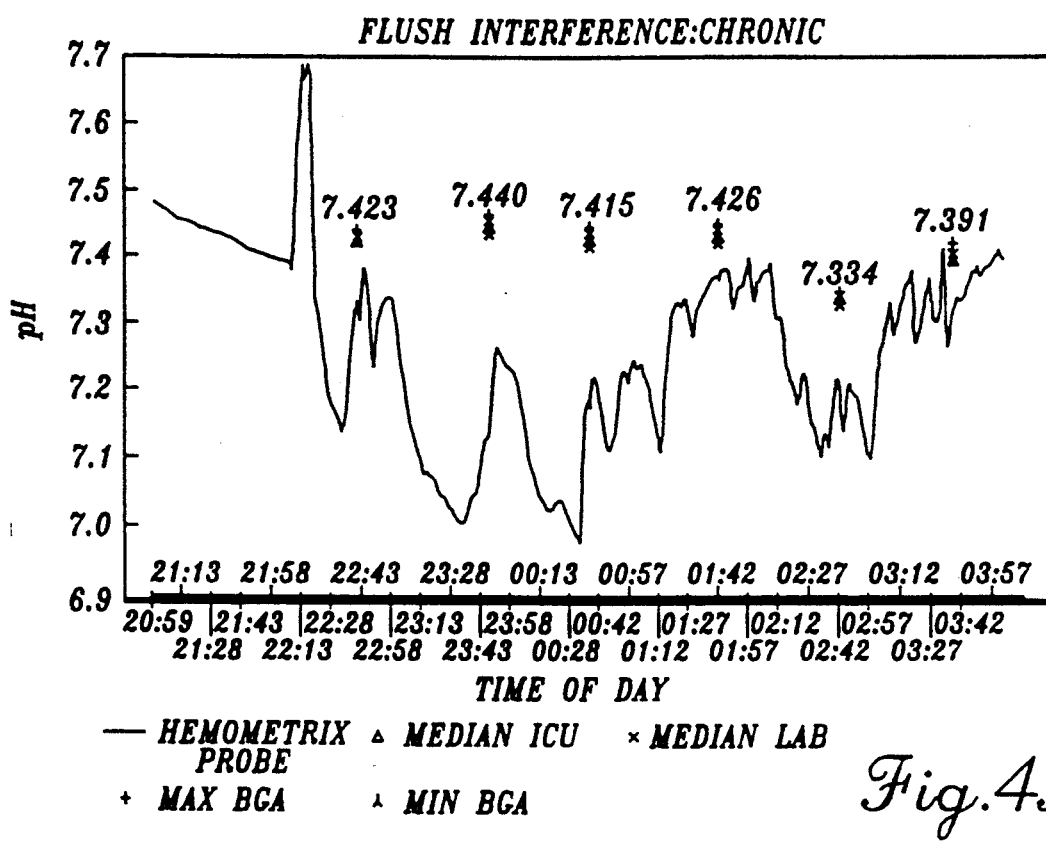
FIGS. 4A, 4B, 4C, and 4D are charts showing the effect of chronic flush interference on measured pH, $pCO_2$, $pO_2$, and temperature, respectively, versus time.
Figure 4B:
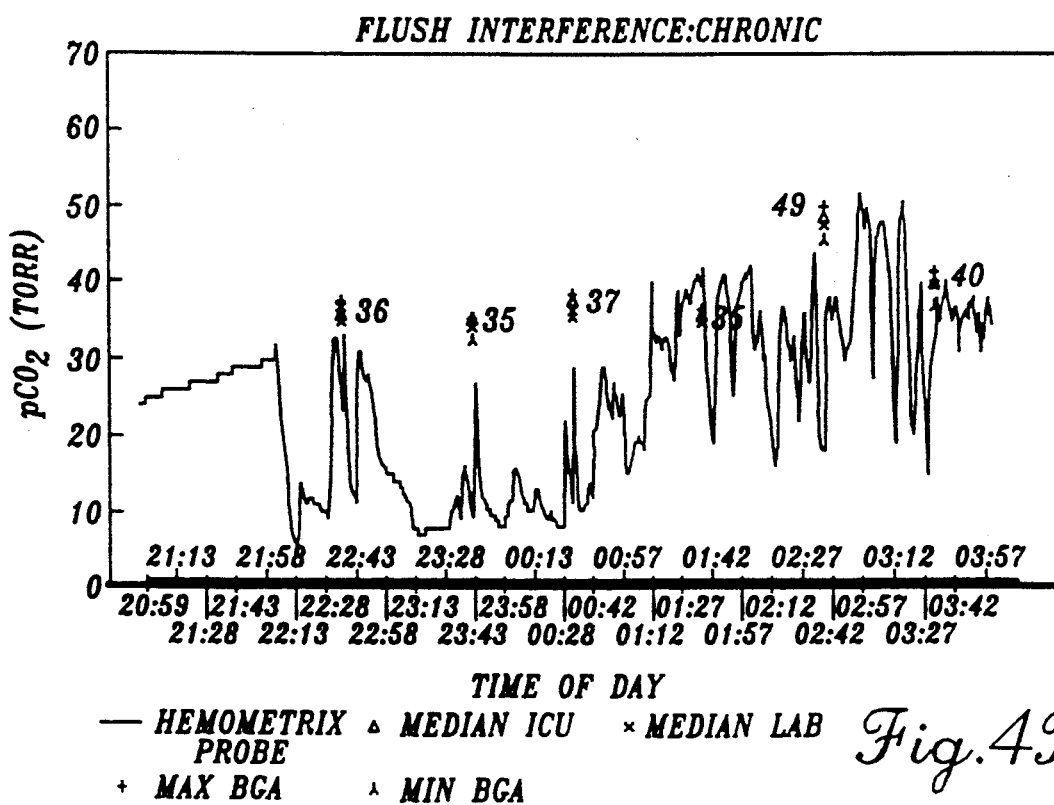
Figure 4C:
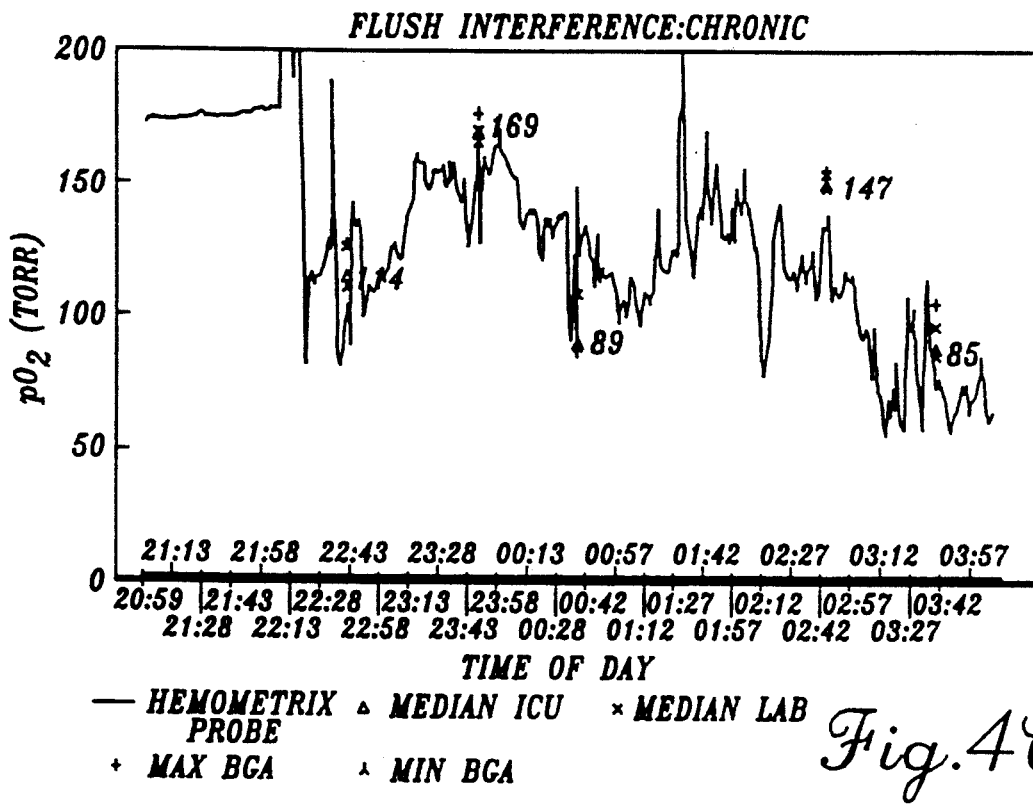
Figure 4D:
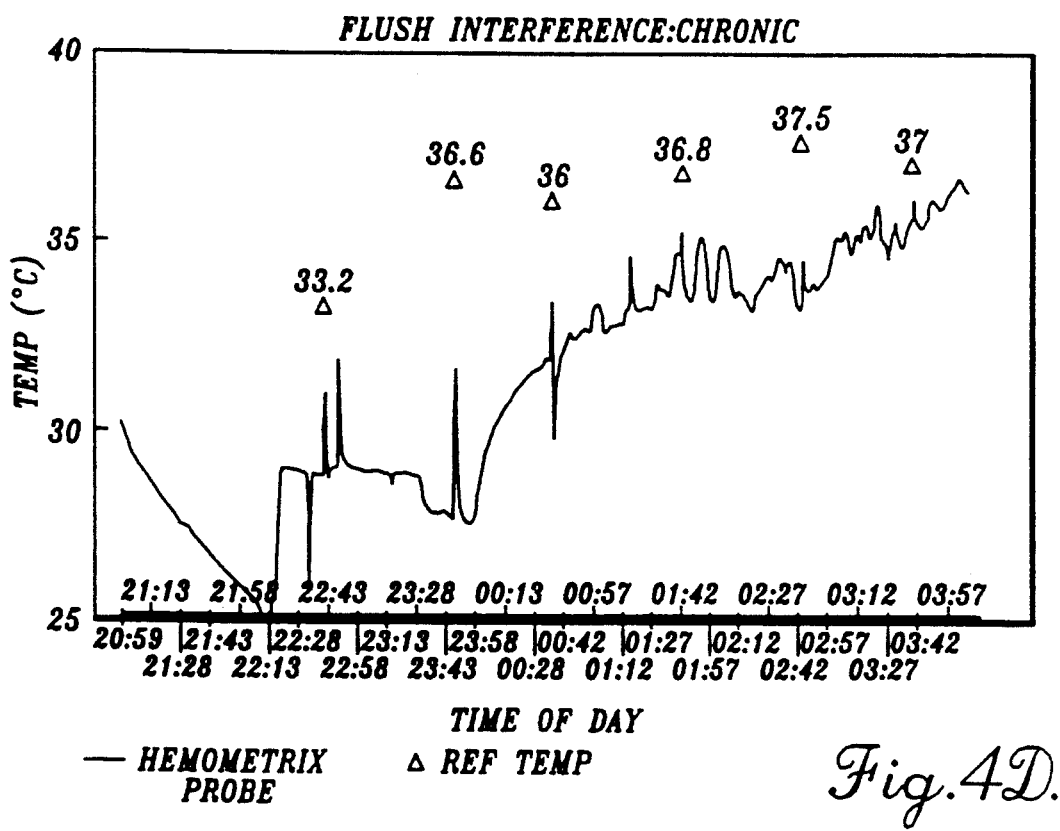
Figure 5A:
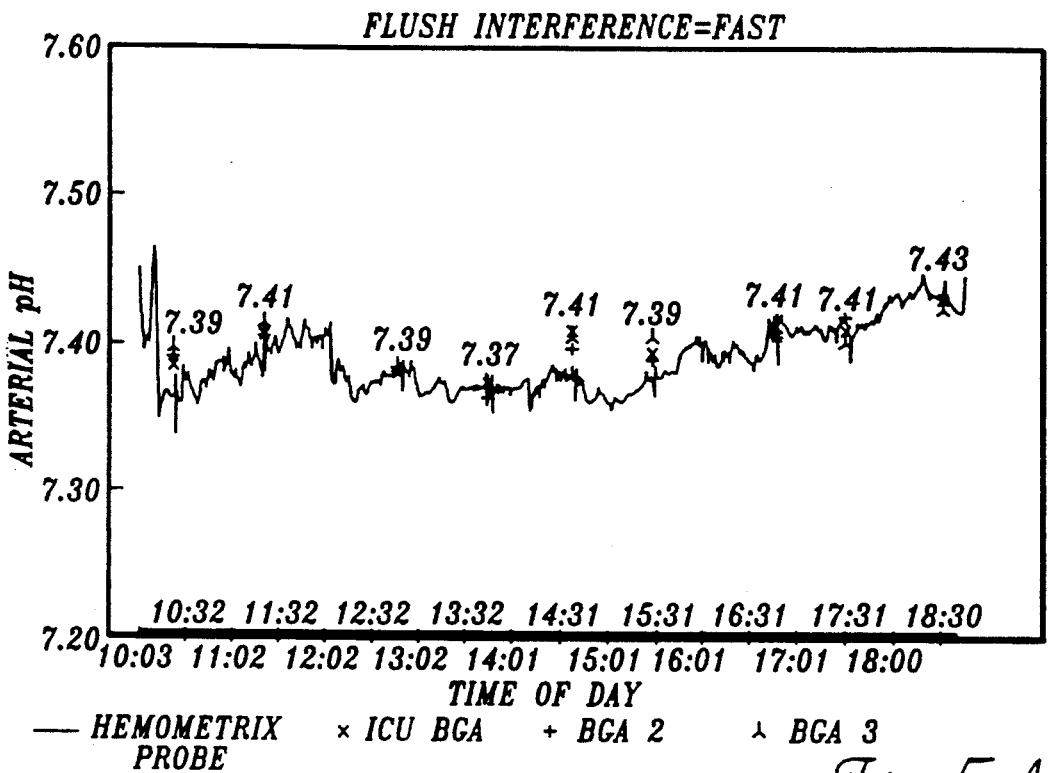
FIGS. 5A, 5B, 5C, and 5D are charts showing the effect of rapid flush interference on measured pH, $pCO_2$, $pO_2$, and temperature, respectively, versus time.
Figure 5B:
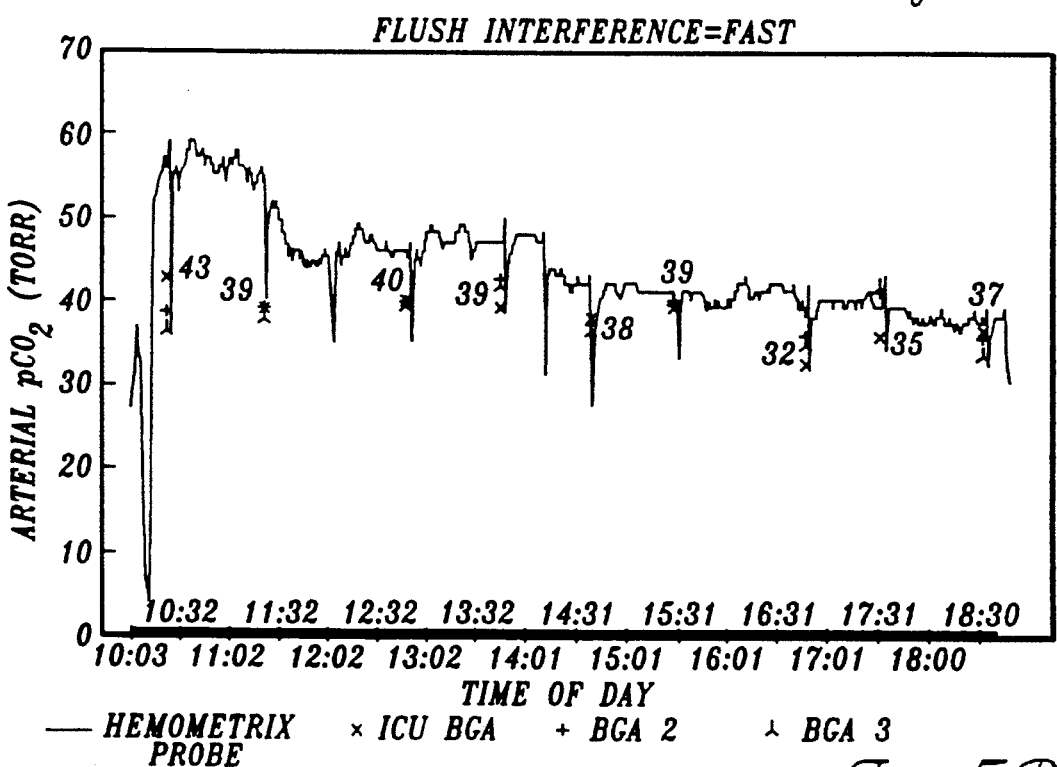
Figure 5C:
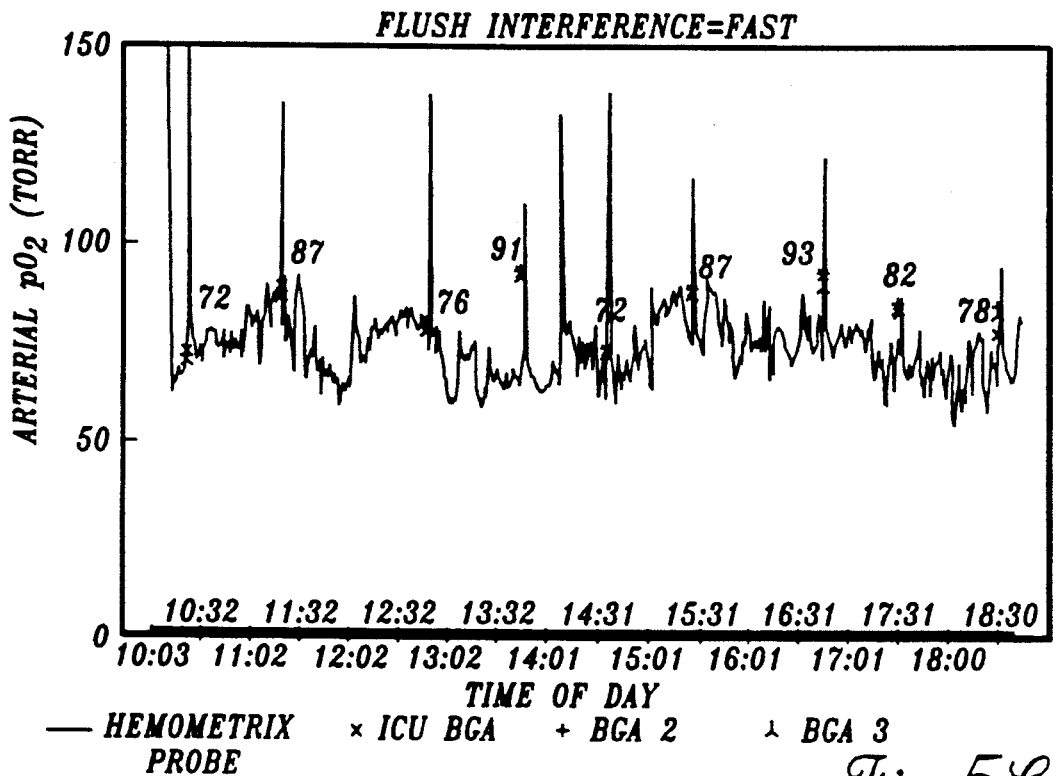
Figure 5D:
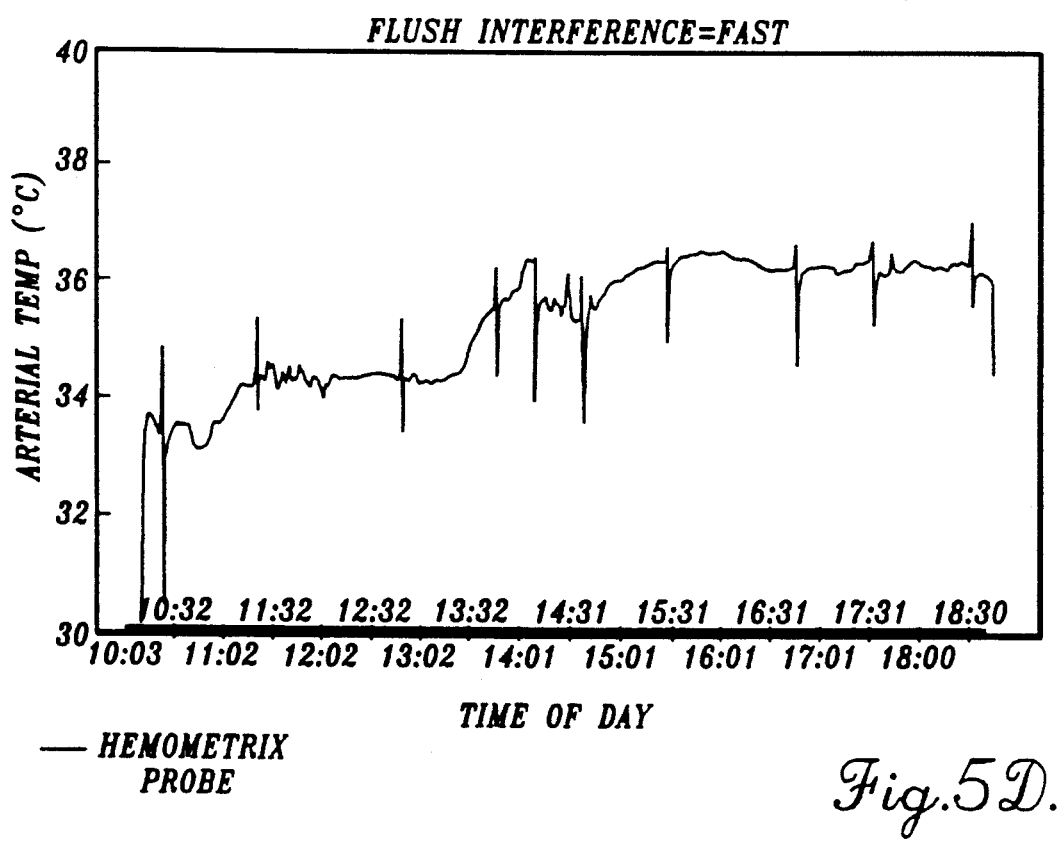

While this method has been found by the inventor to work well for cases where blood flow is intermittently affected by flush interference, it does not identify cases where blood flow is compromised for significant periods of time, such as during chronic flush interference (FIGS. 4A and 4B). It has been discovered that base excess values determined using pCO₂ and pH parameters measured by probe 12 can be used to identify both the "transient" (i.e., intermittent) and chronic periods of flush interference. The base excess of blood, also referred to as the in vitro base excess or base deficit, is defined as the titratable base of blood, and is determined in principal by titration of blood with strong acid or base, to a plasma pH of 7.40, with pCO₂ at 40 torr, at a temperature of 37° C. TENTATIVE STANDARD FOR DEFINITIONS OF QUANTITIES AND CONVENTIONS RELATED TO BLOOD pH AND GAS ANALYSIS, National Committee for Clinical Laboratory Standards, Vol. 2, No. 10, p. 345 (1982). Base excess is a measure of the change in blood from the physiological buffered norm. Because saline flush solution has no buffering capacity, a dilute mixture of systemic blood and flush solution results in a base excess that is not within the physiological norm.

Several formulas for computing base excess are known and accepted in this art and can be used for determining base excess in accordance with one step of the present invention. One suitable equation for calculating base excess is set forth below:

$$BE = (1 - 0.004 \, Hb) \cdot [(HCO_3 - 24) + (9.5 + 1.63 Hb)] \cdot (pH - 7.4) \quad (1)$$

wherein:
BE = base excess meq/ml
pH = measured pH, torr
pCO₂ = measured pCO₂, torr
Hb = hemoglobin concentration, assumed constant at 14 gm/dl
$HCO_3 = 0.031 \cdot pCO_2 - 10^{(pH-6.1)}$ i.e., the concentration of bicarbonate.

Figure 6:
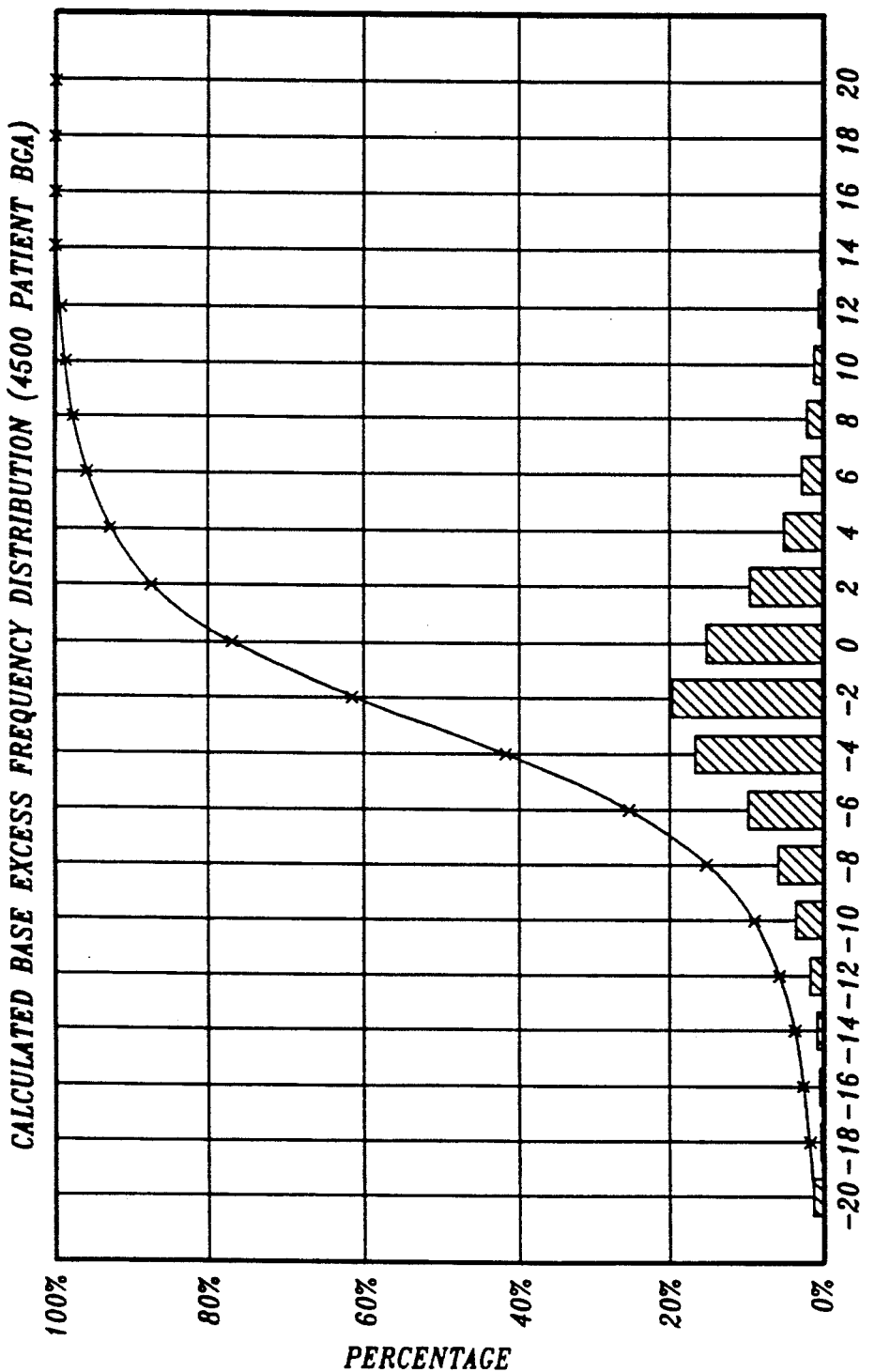
FIG. 6 is a graph showing the frequency distribution of calculated base excess resulting from the blood gas analysis of 4,500 patients.

FIG. 6 presents a distribution histogram of base excess values determined from a data base of 4500 clinical blood gas and pH values obtained from discrete blood gas analysis. As shown in FIG. 6, less than 5% of the blood gas samples had pH and pCO₂ values that produced base excess values of less than −10 meq/ml. A threshold base excess value, such as −10 meq/ml, is thus preferably chosen to identify chronic, or long-term, clinical periods of flush interference.

Figure 7:
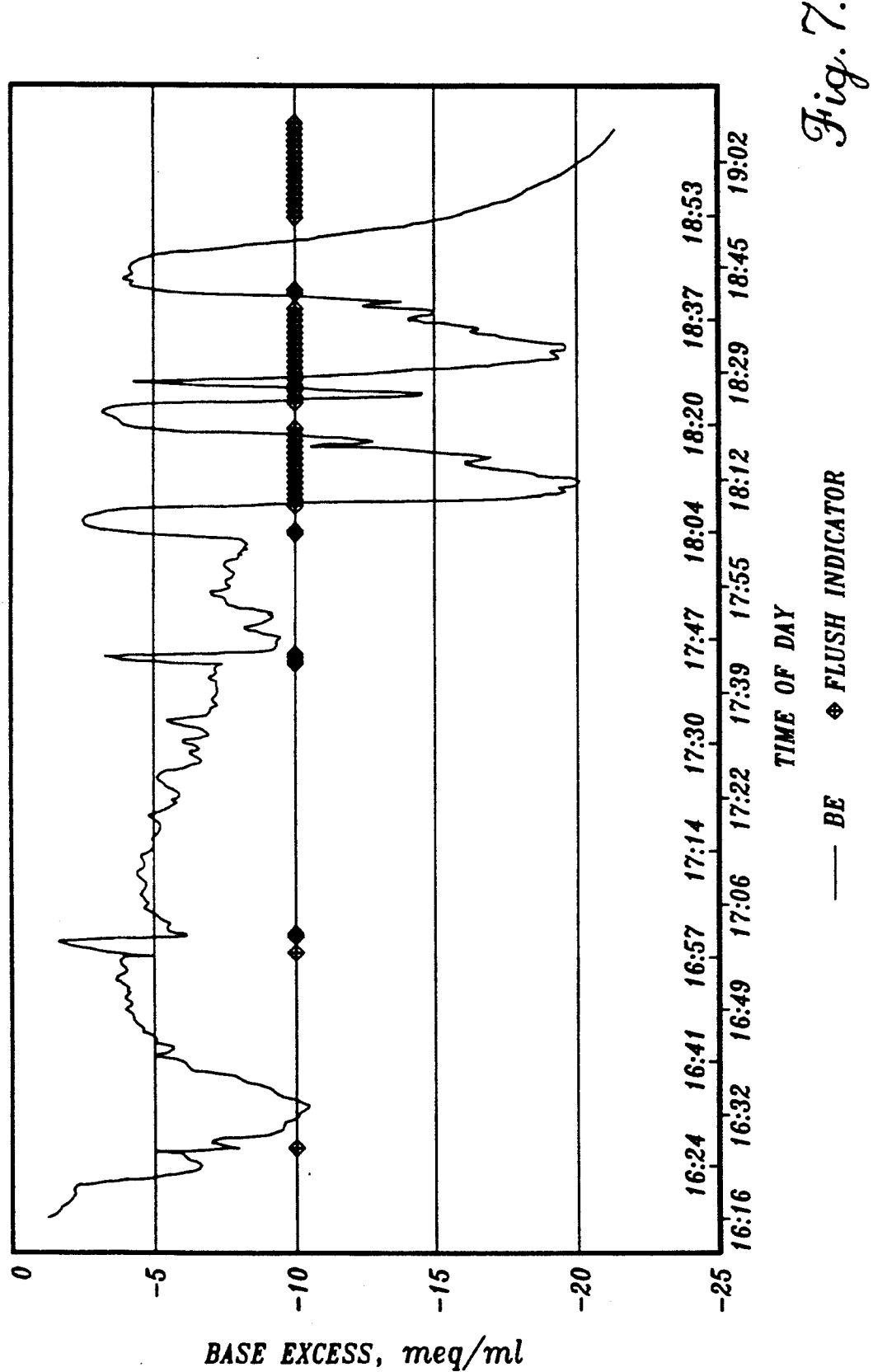
FIG. 7 is a chart showing base excess calculated from measured analyte parameters versus time of day for a patient, including marked indications of flush interference, produced using the system and method of the present invention.

The effectiveness of this procedure is illustrated in FIG. 7, which provides a chart of the base excess determined using measured pH and pCO₂ from probe 12 versus time of day. A flush indicator marking is present on the chart whenever the base excess was found to be less than (i.e., more negative than) the threshold base excess of −10 meq/ml.

A base excess threshold cutoff of −10 meq/ml is used in the preferred embodiment of the present invention, i.e., all calculated base excess values below −10 meq/ml are identified as instances of chronic flush interference. However, it should be understood that the −10 meq/ml threshold is a somewhat arbitrary cutoff, and other thresholds, such as −12 meq/ml or −14 meq/ml, could also be successfully used in practicing the present invention.

The use of a threshold base excess cutoff has been found to be extremely effective for identifying long duration flush interference occurrences, but is less successful at accurately identifying periods of variable flush interference and for identifying the onset of flush interference. To identify the onset of flush interference and also, the more dynamic periods of flush interference, the time rate of change or first derivative of base excess has been found usable as an absolute indicator. The time rate of change of base excess is determined as follows:

$$dBE_t/dt = [BE_t - BE_{(t-2)}]/[t-2)] \quad (2)$$

wherein:
t = time, in minutes
dBE/dt = time rate of change of base excess at time t, meq/ml/min
$BE_t$ = the base excess value determined using measured pH and pCO₂ at time t, meq/ml
$BE_{(t-2)}$ = the base excess value calculated using measured pH and pCO₂ at a time t−2 minutes, meq/ml.

Figure 8:
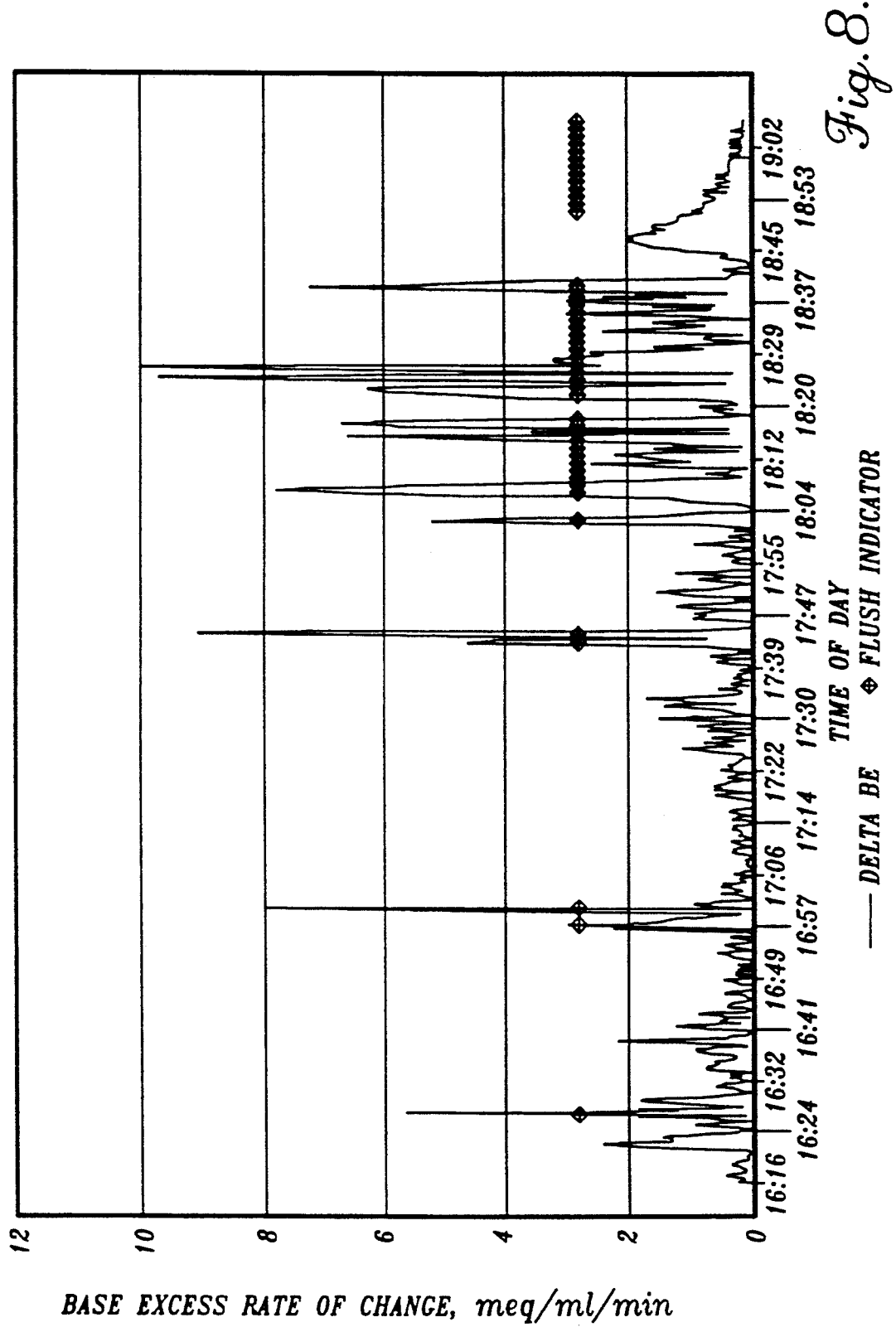
FIG. 8 is a chart of the time rate of change of base excess, calculated based on measured chemical analyte parameters, versus time of day for a patient, including indications of flush interference, produced by the system and method of the present invention.

It has been found that an absolute value of the time rate of change of base excess (determined using measured pH and pCO₂ from probe 12) that is greater than 2.8 meq/ml/min accurately identifies the onset of flush interference and dynamic periods of flush interference. FIG. 8 provides a chart of the absolute value of the time rate of change of base excess determined using measured pH and pCO₂ as a function of time of day. Flush indicator markings on the chart indicate periods of time when the rate of change exceeded the threshold value, indicating flush interference.

The threshold cutoff for the time rate of change of base excess noted above, i.e., 2.8 meq/ml/min, is somewhat arbitrary, and it should be apparent to those of ordinary skill in the art that different, but equally suitable threshold values could be chosen within the scope of the present invention.

In practice, system 10 is used to monitor blood gas parameters every ten seconds. The two-minute period used for computation of the time rate of change of base excess in the above-noted Equation (2) may be varied to provide a faster response period. Thus, for example, it has been found preferable to use a 30-second analysis for more rapid identification of the onset of flush interference. In this instance, Equation (2) for computing the time rate of change base excess can be simplified as follows:

$$\Delta BE = |BE_{(t)} - BE_{(t-30)}| \quad (3)$$

wherein:
t = time, in seconds
ΔBE = the absolute value of the change in calculated base excess over 30 seconds, meq/ml
$BE_{(t)}$ = base excess from measured pH and pCO₂ at time t, meq/ml
$BE_{(t-30)}$ = base excess from measured pH and pCO₂ at time (t−30 sec), meq/ml.

From the previously noted threshold cutoff of 2.8 meq/ml/min for the time rate of change of base excess, it can be seen that an absolute change in base excess of greater than 1.4 meq/ml over a 30-second period of time indicates a condition of flush interference in the preferred embodiment.

Thus, periods of flush interference can be identified using the method of the present invention when either: (a) the calculated base excess is less than the threshold base excess of −10 meq/ml; or, (b) the absolute value of the calculated time rate of change of base excess is greater than the threshold of 2.8 meq/ml/min. This two-part test is effective in identifying both periods of chronic interference and periods of intermittent interference and the onset of interference. However, the two-part test has not been found reliably effective at identifying instances of fast flush, when the arterial line is rapidly cleared of blood by the introduction of a bolus of saline, due to the differential response times of the pH and $pCO_2$ sensors on probe 12. It has been found that these instances of fast flush can be identified using the temperature change measured by probe 12 that occurs during fast flush, due to the temperature difference between in vivo blood and ambient saline flush solution. A high rate of change in temperature indicates the onset of a fast flush. The time rate of change, or first derivative of measured temperature is determined as follows:

$$dT_t/dt=[T_t-T_{(t-1)}]/[t-(t-1)] \quad (4)$$

wherein:
$dT_t/dt$ = time rate of change of measured temperature at time t, °C./min.
$T_t$ = measured temperature at time t, °C.
t = time, minutes.

Figure 9:
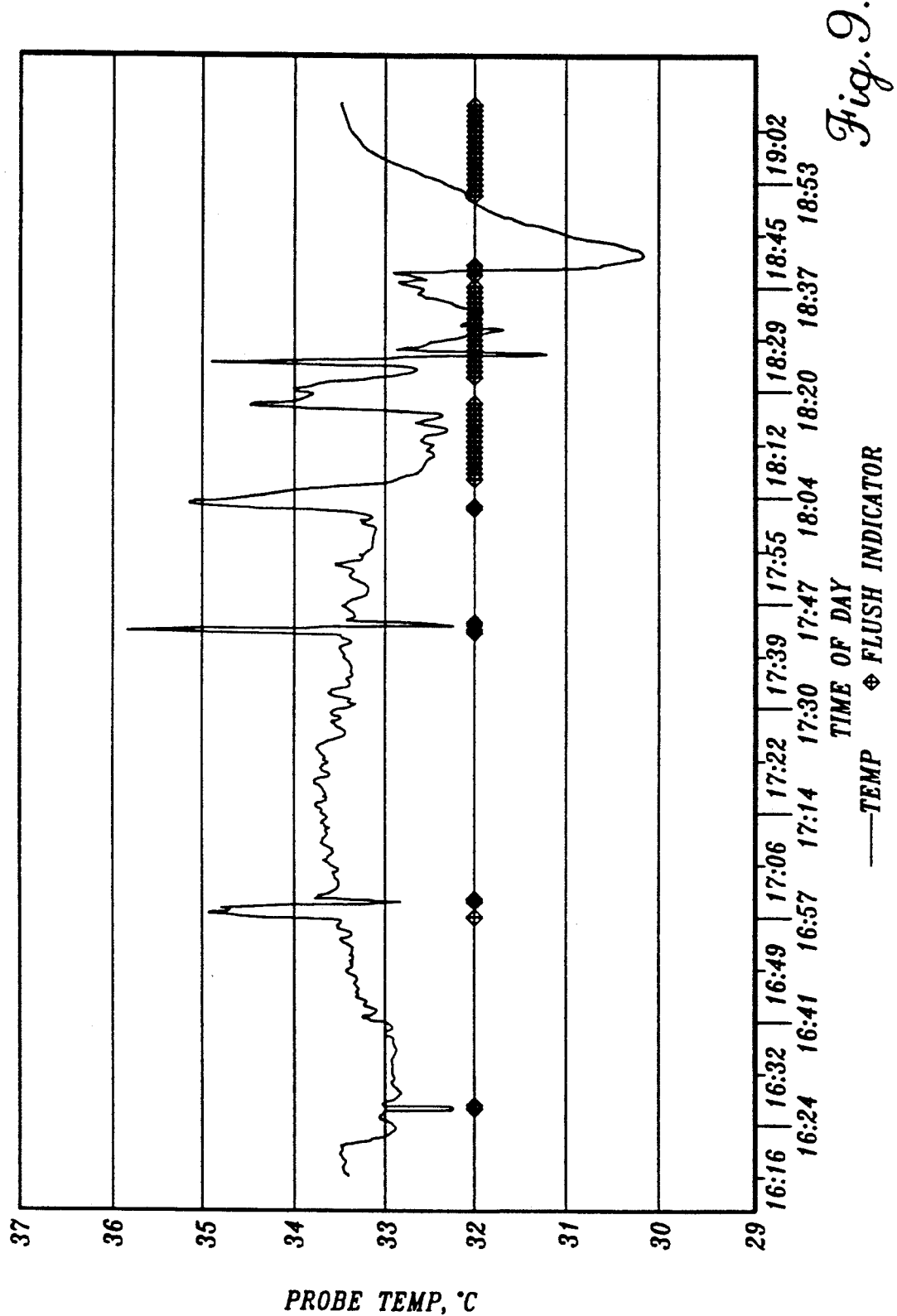
FIG. 9 is a chart of the measured temperature versus time of day for a patient, including indications of flush interference, produced by the method and system of the present invention.

It has been found that an absolute time rate of change of more than 7° C./min. is effective in identifying substantially all fast flushes. FIG. 9 provides a chart of the measured temperature by probe 12 versus time of day. A flush indicator marking is present on the chart whenever the absolute value of the calculated time rate of change of measured temperature was found to exceed the threshold time rate of change of temperature.

Again, in order to provide faster warnings, a shorter sampling time can be used, such as ten seconds. In this case, the absolute change in temperature over a ten-second period can be compared to a threshold value, wherein the absolute temperature change is determined as follows:

$$\Delta T_t = |T_t - T_{(t-10)}| \quad (5)$$

wherein:
$\Delta T_t$ = absolute value of the change in measured temperature over 10 seconds, °C.
$T_t$ = the measured temperature at time t, °C.
$T_{(t-10)}$ = the measured temperature at time (t−10 sec), °C.
t = time, seconds.

From the previously noted threshold for the absolute value for the time rate of change of measured temperature of 7° per minute it should be apparent that an absolute temperature change over a period of 10 seconds greater than a threshold of approximately 1.17° C. identifies a fast flush condition.

In summary, the method of the present invention identifies a condition of flush interference when any one or more of three thresholds is exceeded. Thus, a warning of flush interference is generated when either: (a) the calculated base excess is less than a threshold base excess; (b) the absolute value of the calculated time rate of change of base excess is greater than a threshold time rate of change of base excess; or, (c) the absolute value of the time rate of change of measured temperature is greater than a threshold time rate of change of temperature.

Figure 10:
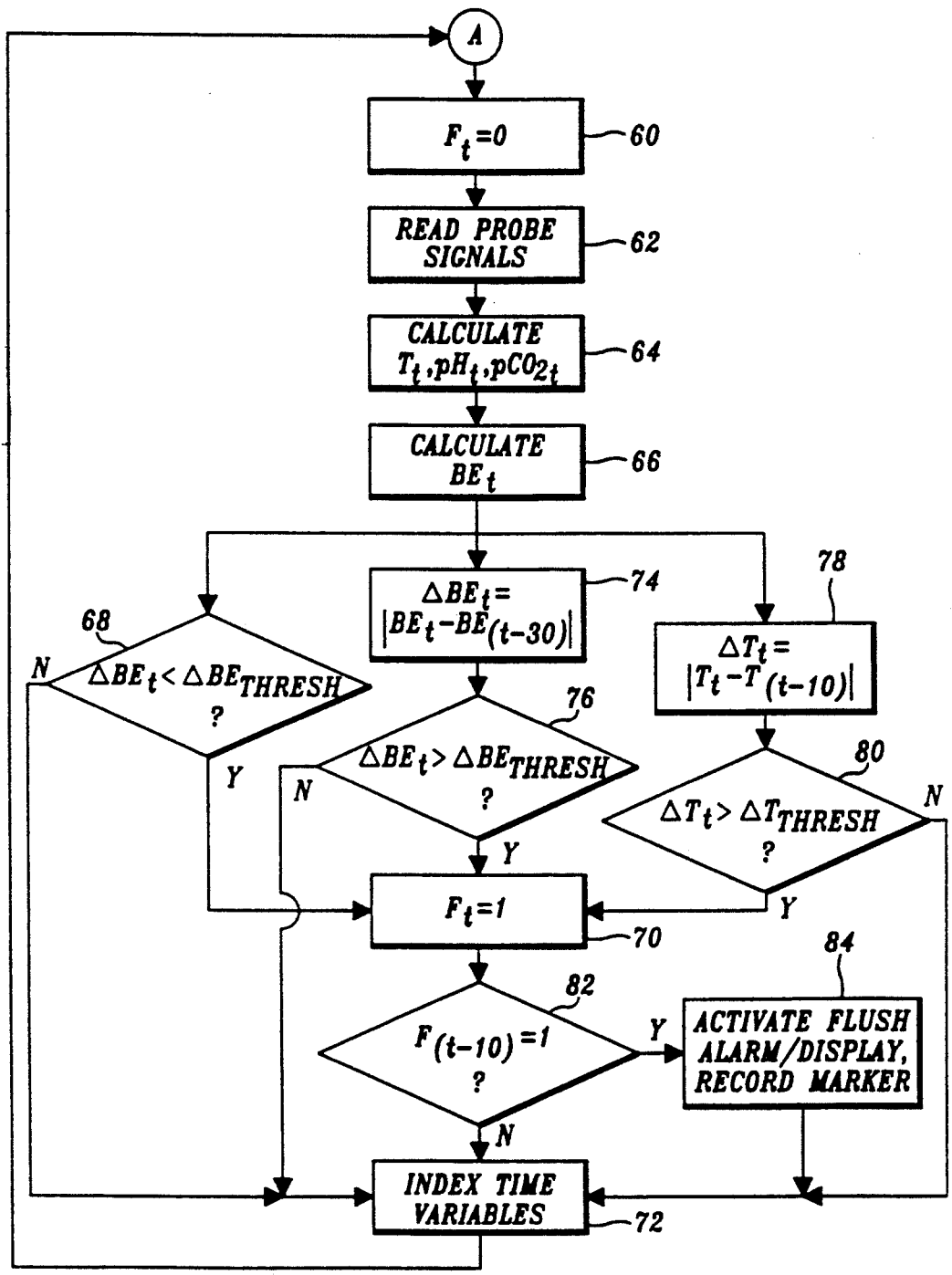
FIG. 10 is a flow diagram illustrating the logical steps implemented to detect flush interference.

A flow chart illustrating the logical steps implement by signal processor 18 (FIG. 1) in determining conditions of flush interference using this three-part test is provided in FIG. 10. The logical steps illustrated are repeated every 10 seconds, at each measurement of blood gas parameters by probe 12 and sensing system 14. At a block 60 of the flow chart, a flush flag $F_t$ is set equal to 0. The light signals from probe 12 are then read by signal processor 18 at a block 62. Signal processor 18 determines the current measured temperature, pH, and $pCO_2$ values in a block 64. Signal processor 18 then determines the current base excess value in a block 66 using Equation (1), as set forth previously. The logic then splits into three branches for processing of each of the three parts of the flush condition test.

In the first of these three branches, the current base excess value is compared with the threshold base excess value in a block 68. If the current base excess value is less than the threshold base excess value (e.g., −10 meq/ml), the flush flag is set to 1 at a block 70. If the current base excess value is not less than the threshold base excess value, this branch of the subroutine proceeds to block 72 to index time variables, as described below.

The second branch of the logic proceeds from block 66 to a block 74 for determination of the current absolute change in base excess value over the previous 30 seconds, using Equation (3). Thus, the absolute change in base excess is determined as the absolute value of the current base excess value minus the base excess value measured 30 seconds previously. The current absolute change in base excess is then compared to the threshold change in base excess (e.g., 1.4 meq/ml) in a block 76. If the current absolute change in base excess is greater than the threshold change in base excess, indicating a flush interference condition may exist, the flush flag $F_t$ is set to one in block 70. If the current change in base excess is not greater than the threshold change in base excess, this branch of the logic proceeds to block 72 for indexing of time variables.

The third branch of the logic proceeds from block 66 to a block 78 for determination of the current absolute change in measured temperature in accordance with Equation (5). The current absolute change in measured temperature is determined as the absolute value of the difference between the current temperature and the temperature measured 10 seconds previously. This branch of the logic then proceeds from block 78 to a block 80, wherein the current absolute change in temperature is compared with a threshold change in temperature (e.g., 1.17° C.). If the current change in absolute temperature is greater than the threshold change of temperature, indicating a flush interference condition may exist, this branch of the logic continues to block 70, wherein the flush flag is set to one. If the current absolute change in measured temperature is not greater than the threshold change in measured temperature, indicating that a flush interference condition does not exist according to this parameter, this branch of the logic proceeds to block 72 for indexing of time variables.

If any one or more of the tests comparing current base excess value (block 68), current time rate of change of base excess (block 76), or current time rate of change of measured temperature (block 80) indicates a condition of flush interference, the flush flag of block 70 is set. The logic then progresses from block 70 to a block 82, wherein the logic determines whether the flush flag was also set in the previous cycle completed 10 seconds earlier. If the flush flag was previously set, one or more indications of flush interference were found during each of two sequential readings of measurements produced by probe 12, and a condition of flush interference can accurately be detected. In this instance, the logic progresses to a block 84, wherein the various alarm devices 20 of FIG. 1 are activated to warn medical personnel that a condition of flush interference currently exists. The logic then proceeds to block 72 for the indexing of time variables.

If none of the three tests indicates a condition of flush interference, each branch of the logic progresses to block 72, skipping blocks 70 and 82, and the flush flag is not set. Likewise, if two successive indications of flush interference have not been determined in block 82, indicating the current reading may be a singular noise artifact rather than a condition of flush interference, the warning alarms alarm devices are not activated in block 84, and the subroutine progresses to block 72. In block 72, the time variables $BE_{(t-30)}$, $T_{(t-10)}$, and $F_{(t-10)}$ are indexed, in a manner that will be apparent to those of ordinary skill in the art. Additionally, a timing loop (not illustrated) holds the logic at this point (block 72) until 10 seconds after the previous reading of signals from probe 12. At that time, the logic loops back to the start at point A, and the current flush flag $F_t$ is reset to 0 in block 60.

If all of the conditions of flush interference are met, based on satisfaction of one or more of the three tests of blocks 68, 74, and 78 for the current test sequence, as well as in the previous test sequence, the various alarm devices 20 of system 10 are activated (block 84). Referring to FIG. 1, when signal processor 18 determines that a condition of flush interference exists, these alarm devices 20 alert medical personnel that the current readings from the probe 12 should be ignored. The alarm devices 20 preferably include a video monitor 90, which is conventionally included in systems for monitoring the progress of in vivo blood gas measurement. When a condition of flush interference is identified by the system 10, an icon is activated on video monitor 90 to warn medical personnel that the current reading then being displayed is affected by flush interference. At the same time, an audible alarm 92 is momentarily sounded to alert medical personnel.

System 10 also includes a record storage memory 94 for storing the results of a blood gas analysis performed by system 10 over a period of time. A flush interference marker can be entered in record storage memory 94 each time a condition of flush interference is detected, creating a record of data points and flush interference markers indicating the data points that should be ignored due to flush interference. Finally, system 10 also includes a hard copy trend graph recorder 96 that records data produced by system 10. A flush indicator marker is preferably printed on the trend graph recorder 96 output each time a condition of flush interference is identified, as shown in the charts of FIGS. 7, 8, and 9.

The logic flow chart of FIG. 10 is provided by way of example. Those of ordinary skill in the art of programming will realize that there are various other ways to implement the method of the present invention. While the preferred embodiment of the invention has been illustrated and described, it will be appreciated that various changes, alterations and substitutions can be made therein without departing from the spirit and scope of the invention. Thus, it is intended that the scope of this invention be limited only by its definitions in the appended claims.

The embodiments of the invention in which an exclusive property or privilege is claimed are defined as follows:

1. A method for detecting an interference during an in vivo measurement of at least one parameter sensed by an indwelling probe, where the interference is caused by introducing a flush fluid proximate said probe, comprising the steps of:
   (a) periodically measuring at least one parameter using the indwelling probe, an accuracy with which said parameter is measured being affected by the flush fluid, wherein the step of measuring at least one parameter comprises measurement of at least a pH and a $pCO_2$;
   (b) determining a time rate of change of the measured parameter, wherein the step of determining a time rate of change comprises the step of determining a time rate of change of a base excess value calculated using the measured pH and the measured $pCO_2$;
   (c) comparing the time rate of change of the measured parameter with a predefined threshold time rate of change; and
   (d) activating a warning device if the time rate of change of the measured parameter exceeds the predefined threshold time rate of change to indicate that the flush fluid has substantially affected the accuracy with which the parameter has been measured.

2. The method of claim 1, wherein:
   (a) an absolute value of the time rate of change of the base excess is determined; and
   (b) the step of comparing the calculated time rate of change comprises the step of comparing the absolute value of the time rate of change of the base excess to a predefined threshold time rate of change of the base excess.

3. The method of claim 2, further comprising the step of comparing the calculated base excess to a threshold base excess, wherein the step of activating the warning device comprises the step of activating the warning output device if either:
   (a) the absolute value of the time rate of change of the base excess exceeds the threshold time rate of change of the base excess; or
   (b) the calculated base excess is less than the threshold base excess.

4. The method of claim 3, further comprising the steps of:
   (a) periodically measuring a temperature with the probe;
   (b) determining an absolute value of a time rate of change of the measured temperature;
   (c) comparing the absolute value of the time rate of change of the measured temperature to a predefined threshold time rate of change of the temperature; and
   (d) activating the warning device if either:
      (i) the base excess is less than the predefined threshold base excess;
      (ii) the absolute value of the time rate of change of the base excess exceeds the predefined threshold time rate of change of the base excess; or
      (iii) the absolute value of the time rate of change of the measured temperature exceeds the predefined threshold time rate of change of temperature.

5. The method of claim 2, further comprising the steps of:
   (a) periodically measuring a temperature with the probe;

(b) determining an absolute value of the time rate of change of the measured temperature;

(c) comparing the absolute value of the time rate of change of the measured temperature to a predefined threshold time rate of change of temperature; and (d) activating the warning device if either:
  (i) the absolute value of the time rate of change of the base excess exceeds the predefined threshold time rate of change of the base excess; or
  (ii) the absolute value of the time rate of change of the measured temperature exceeds the predefined threshold time rate of change of temperature.

6. The method of claim 1, wherein:
(a) the step of measuring at least one parameter further comprises the step of measuring a temperature;
(b) the step of determining a time rate of change further comprises the step of determining an absolute value of the time rate of change of the measured temperature;
(c) the step of comparing comprises the step of comparing the absolute value of the time rate of change of the measured temperature with a predefined threshold time rate of change of temperature; and
(d) the warning device is activated if the absolute value of the time rate of change of the measured temperature is greater than the predefined threshold time rate of change of temperature.

7. The method of claim 6, wherein the step of measuring at least one parameter further comprises the step of measuring a pH and a partial pressure of carbon dioxide, further comprising the steps of:
(a) determining a base excess value; and
(b) comparing the base excess value to a predefined threshold base excess value, wherein the step of activating the warning device comprises the step of activating the warning device if either:
  (i) the base excess value is less than the predefined threshold base excess; or
  (ii) the absolute value of the time rate of change of the measured temperature exceeds the predefined threshold time rate of change of temperature.

8. A method for detecting an interference during the in vivo measurement of a parameter using an indwelling probe, where said interference is caused by introducing a flush fluid proximate said probe, comprising the steps of:
(a) periodically measuring a pH and a $pCO_2$ using said probe;
(b) determining a base excess value using the measured pH and measured $pCO_2$;
(c) comparing the base excess value to a predefined threshold base excess; and
(d) activating a warning device if the base excess value is less than the predefined threshold base excess.

9. The method of claim 8, further comprising the steps of:
(a) determining an absolute value of the time rate of change of the base excess value;
(b) comparing the absolute value of the time rate of change of base excess to a predefined threshold time rate of change of base excess; and
(c) activating the warning device if either:
  (i) the base excess value is less than the predefined threshold base excess; or
  (ii) the absolute value of the time rate of change of the base excess exceeds the predefined threshold time rate of change of the base excess.

10. The method claim 9, further comprising the steps of:
(a) periodically measuring a temperature with the probe;
(b) determining an absolute value of the time rate of change of the measured temperature;
(c) comparing the absolute value of the time rate of change of the measured temperature to a predefined threshold time rate of change of the temperature; and
(d) activating the warning device if either:
  (i) the base excess value is less than the predefined threshold base excess;
  (ii) the absolute value of the time rate of change of the base excess exceeds the predefined threshold time rate of change of the base excess; or
  (iii) the absolute value of the time rate of change of the measured temperature excess the predefined threshold time rate of change of temperature.

11. A method for detecting an interference during an in vivo measurement of a parameter using an indwelling probe, where said interference is caused by introducing a flush fluid proximate said probe, comprising the steps of:
(a) periodically measuring a temperature with the probe;
(b) determining an absolute value of the time rate of change of the measured temperature;
(c) comparing the absolute value of the time rate of change of the measured temperature with a predefined threshold time rate of change of temperature; and
(d) activating a warning device if the absolute value of the time rate of change of measured temperature is greater than the predefined threshold time rate of change of temperature.

12. In a system for in vivo monitoring a plurality of parameters of a patient's blood, apparatus for providing a warning when a flush fluid interferes with the accuracy with which said plurality of parameters are monitored, comprising:
(a) a probe for sensing a pH and a $pCO_2$ in the blood, producing a pH signal and a $pCO_2$ signal that are respectively indicative thereof;
(b) means coupled to the probe to receive the pH and $pCO_2$ signals, for determining a measured pH and measured $pCO_2$ in response to said signals, and for determining a base excess value using the measured pH and measured $pCO_2$;
(c) means for comparing the base excess value to a predefined threshold base excess;
(d) a warning device; and
(e) means for activating the warning device if the base excess value is less than the predefined threshold base excess.

13. The system of claim 12, further comprising:
(a) means for determining an absolute value of the time rate of change of the base excess value;
(b) means for comparing the absolute value of the time rate of change of the base excess value to a predefined threshold time rate of change of the base excess; and (c) the means for activating the warning device do so if either:
  (i) the base excess value is less than the predefined threshold base excess; or
  (ii) the absolute value of the time rate of change of the base excess value is greater than the predefined threshold time rate of change of the base excess.

14. The system of claim 13, wherein the probe includes a temperature sensor, further comprising:
  (a) means for computing an absolute value of the time rate of change of measured temperature;
  (b) means for comparing the absolute value of the time rate of change of measured temperature with a predefined threshold time rate of change of temperature; and
  (c) the means for activating the warning device do so if either:
    (i) the base excess value is less than the predefined threshold base excess;
    (ii) the absolute value of the time rate of change of the base excess value is greater than the predefined threshold time rate of change of the base excess value; or
    (iii) the absolute value of the time rate of change of measured temperature is greater than the predefined threshold time rate of change of temperature.

15. The system of claim 12, wherein the probe further comprises a temperature sensor, further comprising:
  (a) means for determining an absolute value of the time rate of change of measured temperature;
  (b) means for comparing the absolute value of the time rate of change of measured temperature with a predefined threshold time rate of change of temperature; and
  (c) the means for activating the warning device do so if either:
    (i) the base excess value is less than the predefined threshold base excess; or
    (ii) the absolute value of the time rate of change of measured temperature is greater than the predefined threshold time rate of change of temperature.

16. A method for detecting an interference during an in vivo measurement of at least one parameter sensed by an indwelling probe, where the interference is caused by introducing a flush fluid proximate said probe, comprising the steps of:
  (a) periodically measuring at least one parameter using the indwelling probe, an accuracy with which said parameter is measured being affected by the flush fluid, wherein the step of measuring at least one parameter comprises measurement of a pH;
  (b) determining a time rate of change of the measured parameter, wherein the step of determining a time rate of change comprises determining the time rate of change of the measured pH;
  (c) comparing the time rate of change of the measured parameter with a predefined threshold time rate of change; and
  (d) activating a warning device if the time rate of change of the measured parameter exceeds the predefined threshold time rate of change to indicate that the flush fluid has substantially affected the accuracy with which the parameter has been measured.

* * * * *

UNITED STATES PATENT AND TRADEMARK OFFICE
CERTIFICATE OF CORRECTION

PATENT NO. : 5,304,495
DATED : April 19, 1994
INVENTOR(S) : J. B. Yim

It is certified that error appears in the above-indentified patent and that said Letters Patent is hereby corrected as shown below:

| COLUMN | LINE | |
|---|---|---|
| 1 | 63 & 64 | "rele-vent" should read --relevant-- |
| 2 | 9 | "trails" should read --trials-- |
| 2 | 31 & 32 | "ensur-ing" should read --ensuing-- |
| 2 | 62 | after "of" insert --change of-- |
| 16 | 23 | "excess" should read --exceeds-- |

Signed and Sealed this

Second Day of August, 1994

Attest:

BRUCE LEHMAN

*Attesting Officer*     *Commissioner of Patents and Trademarks*